United States Patent [19]

Nave et al.

[11] Patent Number: 5,404,218
[45] Date of Patent: Apr. 4, 1995

[54] FIBER OPTIC PROBE FOR LIGHT SCATTERING MEASUREMENTS

[75] Inventors: Stanley E. Nave, Evans, Ga.; Ronald R. Livingston, Aiken, S.C.; William S. Prather, Augusta, Ga.

[73] Assignee: The United States of America as represented by the United States Department of Energy, Washington, D.C.

[21] Appl. No.: 154,353

[22] Filed: Nov. 18, 1993

[51] Int. Cl.6 .................... G01J 3/44; G01N 21/65
[52] U.S. Cl. ..................... 356/301; 356/246; 356/307
[58] Field of Search .............. 356/301, 307, 244, 246

[56] References Cited

U.S. PATENT DOCUMENTS

| | | |
|---|---|---|
| 3,906,241 | 9/1975 | Thompson ............... 356/301 |
| 4,784,486 | 11/1988 | Van Wagenen et al. ........ 356/301 |
| 4,802,761 | 2/1989 | Bowen et al. ............ 356/301 |
| 4,857,472 | 8/1989 | Wolfbeis ............... 422/58 X |
| 4,892,383 | 1/1990 | Klainer et al. . |
| 5,112,127 | 5/1992 | Carrabbo et al. .......... 356/301 |
| 5,124,129 | 6/1992 | Riccitelli et al. .......... 422/58 X |
| 5,139,334 | 8/1992 | Clarke ................. 356/301 |
| 5,341,206 | 8/1994 | Pittaro et al. ........... 356/301 |

FOREIGN PATENT DOCUMENTS

WO87/06011 10/1987 WIPO ............... 356/301

*Primary Examiner*—F. L. Evans
*Attorney, Agent, or Firm*—Brian R. Tumm; Harold M. Dixon; William R. Moser

[57] ABSTRACT

A fiber optic probe and a method for using the probe for light scattering analyses of a sample. The probe includes a probe body with an inlet for admitting a sample into an interior sample chamber, a first optical fiber for transmitting light from a source into the chamber, and a second optical fiber for transmitting light to a detector such as a spectrophotometer. The interior surface of the probe carries a coating that substantially prevents non-scattered light from reaching the second fiber. The probe is placed in a region where the presence and concentration of an analyte of interest are to be detected, and a sample is admitted into the chamber. Exciting light is transmitted into the sample chamber by the first fiber, where the light interacts with the sample to produce Raman-scattered light. At least some of the Raman-scattered light is received by the second fiber and transmitted to the detector for analysis. Two Raman spectra are measured, at different pressures. The first spectrum is subtracted from the second to remove background effects, and the resulting sample Raman spectrum is compared to a set of stored library spectra to determine the presence and concentration of the analyte.

20 Claims, 3 Drawing Sheets

FIBER OPTIC PROBE FOR LIGHT SCATTERING MEASUREMENTS

BACKGROUND OF THE INVENTION

1. Field of the Invention

The present invention relates to fiber optic probes for spectrophotometric analyses of scattered light. More particularly, the present invention relates to fiber optic probes for Raman spectroscopy of gaseous samples. The United States Government has rights in this invention pursuant to Contract No. DE-AC09-89SR18035 between the U.S. Department of Energy and Westinghouse Savannah River Company.

2. Discussion of Background:

Spectrophotometric techniques based on emission, absorption or scattering processes are frequently used for qualitative and quantitative analyses. The development of lasers and optical fibers has allowed the placement of sensitive equipment in locations remote from industrial process environments, making spectrophotometry applicable to a wide range of processes. Applications include on-line monitoring of industrial process streams, monitoring the contents of storage tanks, detection of toxic or explosive substances, studying the migration of subsurface contaminants, and monitoring air and water quality. Where measurements must be made at many different locations, a number of probes may be connected to a single remotely-located measuring instrument by optical fibers, as in the on-line process control monitoring system disclosed in commonly-assigned U.S. Pat. No. 5,131,746. Remote monitoring is essential in harsh chemical and radioactive environments.

Detection of hydrogen is a problem in many industrial process environments. Measurements of hydrogen concentration in the offgas of many chemical processes are used to detect potentially-explosive concentrations so that deflagrations can be prevented. Presently available hydrogen sensors have short lifetimes in corrosive environments, for example, when exposed to acids in an offgas stream. Also, the presence and variabilities of the concentrations of other gases such as carbon dioxide and nitrogen dioxide cause problems in detection and quantification. The large thermal conductivities of these gas mixtures coupled with their varying concentrations preclude the use of thermal conductivity sensors. High concentrations of nitrogen dioxide interfere with or poison currently available electrochemical sensors. Analytical techniques such as gas chromatography and mass spectrometry are capable of detecting hydrogen, however, these techniques require complex equipment that may be difficult or impossible to maintain when placed in a severe process environment, and neither is suited for remote measurements. Remote monitoring using spectrophotometric techniques and an in-situ fiber optic probe would allow detection of hydrogen—and other gases—in severe process environments.

The composition of a sample can often be determined from its absorption spectrum, that is, the frequency or wavelength distribution of the light absorbed by the sample. A typical system for absorption spectroscopy includes a light source, an optical probe containing light-transmitting and light-receiving fibers, and a detector. Light from the source is directed to the sample by the transmitting fiber, passes through the sample, and is transmitted to the detector by the receiving fiber. Measurements taken from a suitable reference sample are compared to measurements taken from the test sample to help determine the concentrations of various constituents in the test sample.

Absorption spectroscopy is useful for detecting and characterizing those analytes that have useful spectra in the ultraviolet (UV), visible (VIS) or near-infrared (near-IR) range. However, many analytes of interest, including hydrogen ($H_2$), oxygen ($O_2$), nitrogen ($N_2$), methane ($CH_4$), carbon dioxide ($CO_2$) and carbon monoxide (CO), do not have any UV-VIS absorption lines; the "fingerprint" regions of the absorption spectra are in the IR range. Because presently-available optical fibers severely attenuate IR wavelengths, absorption spectroscopy is not suitable for remote detection of such analytes.

Optical techniques based on other mechanisms such as fluorescence, luminescence and Raman scattering may be used for detection. Raman spectroscopy is a sensitive analytical technique based on the inelastic scattering of light (typically, monochromatic light frown a laser) by a molecule. The rotational or vibrational energy of a molecule is changed as it is excited to a different energy level by the incident light. The transition to a final energy level is accompanied by emission of radiation. Thus, in addition to elastically-scattered light having the same wavelength as the exciting light, the scattered light contains small amounts of light with different wavelengths. When expressed in terms of the delta wave number (the difference between the laser wavelength and the wavelengths of the scattered light), a Raman spectrum consists of a series of lines starting close to the laser line and corresponding to the possible vibrational or rotational quantum numbers of the sample molecules. The spectrum is characteristic of the scattering molecules, with the intensities of the lines depending on the concentrations of the scattering molecules in the sample.

Vibrational and rotational Raman spectra are typically in the visible or near-IR region, therefore, Raman spectra are less severely attenuated than IR absorption spectra by transmission over optical fibers. In addition, Raman spectroscopy is particularly useful for identifying the constituents of a sample since Raman spectra contain more spectral lines, and sharper lines than obtained with other types of spectroscopy.

A major problem in Raman spectroscopy and other light scattering measurements is the low signal-to-noise ratio, that is, the very low intensity of the Raman-scattered light compared to the intensity of the exciting light. Raman spectroscopy, like absorption spectroscopy, is carried out with a light source, an optical probe, and a detector. Some of the exciting light—and some elastically-scattered light—is reflected back to the light-receiving fibers by the interior surfaces of the probe. Sensitive detectors with high light gathering power and high stray light rejection are needed to isolate and measure the low intensity Raman signal. Such instruments are costly and delicate, and are not well suited for use in many industrial process environments. Furthermore, monochromatic light transmitted by an optical fiber excites the fiber molecules, causing Raman scattering within the fiber itself. This "self-scattering" or "silica scattering" generates an additional signal that interferes with the Raman signal collected from the sample.

These problems are particularly evident for small samples and gases. The smaller the sample chamber, the more exciting light is reflected towards the light-receiving fibers by the chamber walls, and the more difficult to detect the Raman signal. The fewer the number of sample molecules, the smaller the Raman signal. Increasing the sample pressure provides more scattering molecules and therefore an increased Raman signal, but does not significantly change the amount of non-Raman-scattered light reaching the detector.

To improve the signal-to-noise ratio, filters may be used to remove a narrow band of wavelengths centered on the wavelength of the laser line. Chemometric techniques are used to factor out background noise and identify the signal of interest. However, the intensity of a typical Raman signal is much lower than the intensity of the non-Raman-scattered light reaching the light-receiving fibers. Small samples, such as are desirable in process environments or when dealing with hazardous materials, produce Raman signals that are indistinguishable from background levels even after filtering and data analysis.

Various techniques are available for increasing the amount of light collected by the light-receiving fibers of an optical probe. Thus, lenses may be provided to direct light onto the fibers. The ends of the fibers may be tapered for improved coupling efficiency, as described in commonly-assigned and recently filed patent application Ser. No. 08/056,390 (Fiber Optic Probe Having Fibers With Endfaces Formed For Improved Coupling Efficiency), the disclosure of which is incorporated herein by reference.

Some devices incorporate indicators that exhibit a change in an optical property, such as fluorescence emission, color, and so forth, in response to the sample. For example, Riccitelli, et al. (U.S. Pat. No. 5,124,129) coat the inside of a transparent endotracheal tube or connector with a pit-sensitive dye suspended in a predominantly hydrophilic polymer matrix. Wolfbeis (U.S. Pat. No. 4,857,472) adds a fluorescent indicator to an $SO_2$-permeable polymer and coats the resulting composition onto a solid substrate. When the indicator is brought into contact with a $SO_2$-containing medium, the extent to which fluorescence is quenched is a measure of the $SO_2$ content of the medium. Klainer, et al. (U.S. Pat. No. 4,892,383) describe a reservoir fiber optic chemical sensor having a semipermeable membrane to admit the analyte of interest into the cell body.

Despite the variety of fiber optic probes that are available, there is no known optical probe that addresses the problems posed by Raman scattering measurements of small, gaseous samples: low signal intensity and low signal-to-noise ratio due to interference from exciting light. Such a probe would allow the use of Raman spectroscopy for remote monitoring in a wide range of process environments.

SUMMARY OF THE INVENTION

According to its major aspects and broadly stated, the present invention is a fiber optic probe and a method for using the probe for light scattering analyses of a sample. The probe includes a probe body with an inlet for admitting a sample into an interior sample chamber, a first optical fiber for transmitting light from a source into the chamber, and a second optical fiber (or a plurality of fibers) for receiving light from the chamber and transmitting the light to a detector. The interior surface of the probe carries a coating that substantially prevents elastically-scattered light from reaching the second fiber.

The probe is placed in a region where the presence and concentration of an analyte of interest are to be detected, and a sample is admitted into the chamber. Exciting light is transmitted by the first optical fiber into the sample chamber, where at least a portion of the light interacts with the sample to produce Raman-scattered light. Two Raman spectra are measured, at different sample pressures. The first spectrum is subtracted from the second to remove background effects, then, the resulting sample spectrum is compared to a set of stored calibration data to determine the presence and concentration of the analyte.

An important feature of the present invention is the probe. The design of the probe allows exciting light to interact with a sample to produce Raman-scattered light, but substantially prevents the exciting light from entering the second optical fiber and interfering with the low-intensity Raman signal. The probe is connected to a source of light and a spectrophotometer by optical fibers, allowing remote monitoring in industrial process environments and environmental applications.

Another important feature of the present invention is the coating carried by the interior surface of the sample chamber. The coating absorbs any exciting light that reaches the chamber walls, preventing the light from being reflected back to the second optical fiber. The coating may comprise a mixture of an adhesive and light-absorbing particles such as carbon black, or a rough-surfaced material that "traps" light and prevents the light from reaching the second fiber.

Still another feature of the invention is the method for determining the presence and concentration of an analyte from measurements made with the probe. The sample spectrum is computed by subtracting a first Raman spectrum, measured with the sample at a first pressure, from a second spectrum with the sample at a second pressure. Background effects are discounted since the first spectrum acts as a "reference" or "blank" for the second. The sample spectrum is analyzed using a library of stored calibration data to determine whether an analyte is present, and if present, the concentration of that analyte.

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

Figure 1:
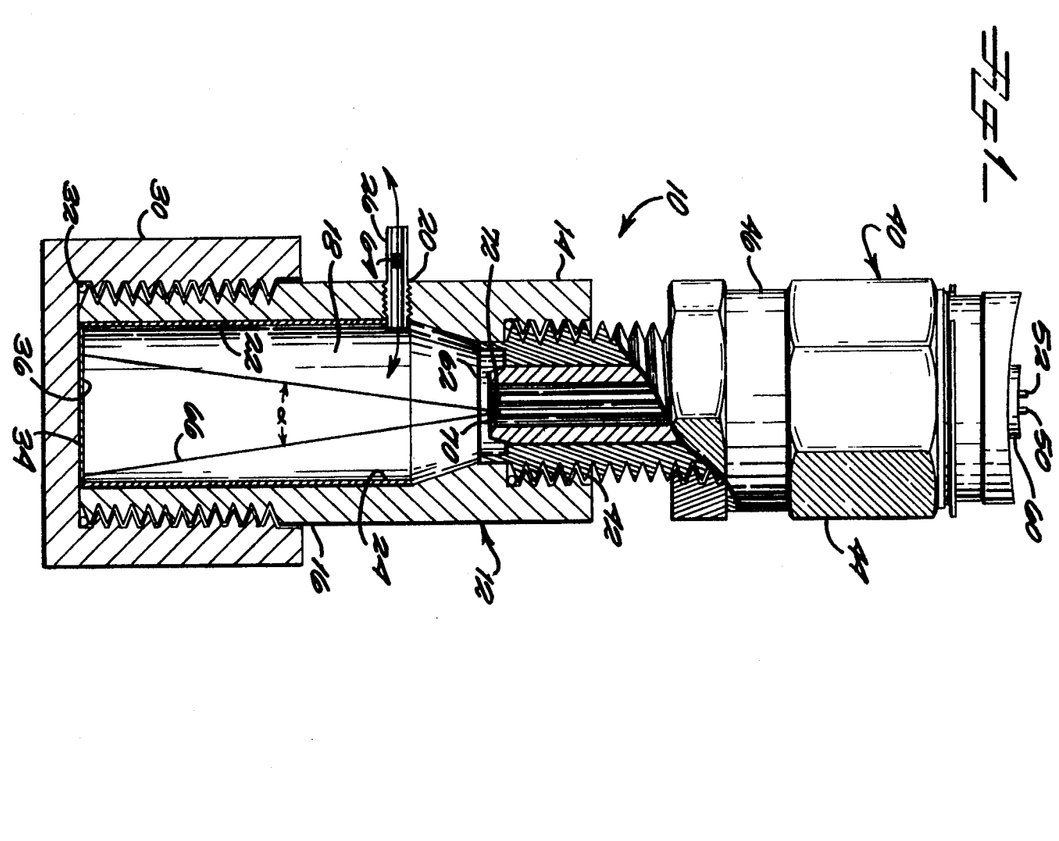
FIG. 1 is a side cross-sectional view of a fiber optic probe according to a preferred embodiment of the present invention.

Referring now to FIG. 1, a fiber optic probe 10 according to a preferred embodiment of the present invention includes a probe body 12 having a proximal end 14 and a distal end 16. Probe body 12 has an interior sample chamber 18, an inlet 20, and an interior surface 22 carrying a coating 24 (to be described below). A threaded fitting 26 is screwed into inlet 20. Alternatively, fitting 26 may be integrally formed with probe body 12, or attached to body 12 by some other means such as welding. Body 12 is preferably a threaded cylinder as shown in FIG. 1, with a length and diameter chosen to provide the desired sample volume in chamber 18.

A threaded cap 30 is screwed onto distal end 16 of probe body 12. If desired, a compression seal 32 such as an O-ring or gasket may be interposed between cap 30 and end 16. An interior surface 34 of cap 30 carries a coating 36. If desired, distal end 16 of body 12 may be closed so that a separate cap 30 is not needed. However, it will be understood that coatings 24 and 36 are readily attached to an open body 12 and a threaded cap as shown in FIG. 1.

A fiber optic terminator 40 is mounted at proximal end 14 of probe body 12. Terminator 40 is preferably a type that maintains optical fibers in a fixed position when terminator 40 is screwed onto body 12, that is, the fibers do not rotate during attachment of terminator 40 to the probe. Thus, terminator 40 may include a threaded union 42, a nut 44, and a barrel 46 adapted for holding optical fibers. Such a terminator prevents damage to the fibers during connection to body 12, and allows easy replacement of the fibers if needed.

When optical measurements are made using optical fibers, it is desirable to maximize the overlap between the area illuminated by a light-transmitting fiber and the area viewed by a light-receiving fiber. Ideally, a single fiber is used for both transmitting and receiving light. This arrangement is not feasible for light scattering measurements such as Raman spectroscopy due to the low intensity of the Raman-scattered light compared to intensity of the non-Raman-scattered light. (As used herein, the term "Raman-scattered light" means inelastically-scattered light having a delta wavelength spectrum about the wavelength of the exciting light. "Non-Raman-scattered light" means the exciting light, and elastically-scattered light of the same wavelength.) Therefore, barrel 46 contains at least two optical fibers, a first, light-transmitting fiber 50 and a second, light-receiving fiber 52. To maximize the areas viewed by fibers 50, 52, the distal ends of fibers 50, 52 are preferably approximately parallel and adjacent to one another within proximal end 14 of probe body 12.

Fiber 50 transmits light from a source, preferably a laser, into sample chamber 18, and fiber 52 receives light from the chamber and transmits the light to a detector such as a spectrophotometer. Fibers 50, 52 may be enclosed by a protective casing 60. To prevent crosstalk between fibers 50 and 52, the fibers may be coated with a light absorbing substance such as carbon black. For example, fibers 50, 52 may be maintained in their relative positions in barrel 46 by means of epoxy mixed with carbon black.

If desired, a plurality of transmitting fibers 50 and a plurality of receiving fibers 52 may be provided. For example, a single fiber 50 might be surrounded by a plurality of fibers 52, preferably bundled with fiber 50 at the center. The greater the number of fibers 52, the greater the signal that can be collected. The ends of fibers 50, 52 may be tapered as described in aforementioned patent application Ser. No. 08/056,390. The optimum numbers of transmitting and receiving fibers depend on the sample to be analyzed, including the constituents of the sample and the concentration of the analyte or analytes of interest.

A window 62 may be provided to protect fibers 50, 52 from contact with the contents of chamber 18. Window 62 is preferably made of a material that is optically transparent in the wavelength range of interest, such as sapphire or silica. If present, window 62 is positioned close enough to the ends of fibers 50, 52 so that direct reflection of exciting light from transmitting fiber 50 to receiving fiber 52 is avoided.

A filter 64 may be positioned in fitting 26. Filter 64, if present, may be a gas-permeable membrane or gas trap for separation of gas species, or some other type of filter that substantially prevents dust, dirt and so forth from entering chamber 18, but allows free flow of the sample gas into the chamber.

Coatings 24 and 36 prevent a substantial portion of non-Raman-scattered light in chamber 18 from reaching fiber 52. As noted above, exciting light interacts with the sample molecules in chamber 18 to produce inelastically-scattered (Raman-scattered) and elastically-scattered light. In addition, some of the exciting light is absorbed by the sample molecules and, in the absence of coatings 24, 26, some is reflected towards fiber 52 by interior surfaces 22, 34, respectively. Coating 36 absorbs a substantial portion, preferably most of the exciting light that passes through chamber 18 without being absorbed or scattered by the sample molecules. Similarly, coating 24 absorbs at least some, and preferably most of the light (both inelastically-scattered Raman light and elastically-scattered light) that reaches it. In a preferred embodiment of the invention, coatings 24 and 36 contain particles of a light-absorbing material, preferably carbon black, mixed with an adhesive such as epoxy. Other light-absorbing materials and adhesives may be used, as long as coatings 24 and 36 absorb light effectively and are substantially nonreactive with the types of samples to be analyzed in probe 10. Coatings 24 and 36 may also take the form of a rough-surfaced material that "traps" light and prevents the light from reaching fiber 52. Together, coatings 24 and 36 substantially reduce the amount of non-Raman-scattered light that is received by fiber 52, thereby increasing the ratio of Raman-scattered light to non-Raman-scattered light reaching fiber 52.

Alternatively, coating 24 is omitted and chamber 18 contains only coating 36. The length of chamber 18 is preferably such that a light cone 66 emitted by fiber 50 does not broaden sufficiently to strike inner surface 22, minimizing internal reflection of laser light by surface 22.

Probe 10 may be made of any suitable materials for the environment of use, preferably materials that are substantially nonreactive with the samples to be analyzed. Thus, probe body 12, end cap 30 and fiber optic terminator 40 may be stainless steel, however, aluminum or plastics such as TEFLON TM might be used for samples that are reactive with stainless steel.

Fibers 50, 52 are preferably single filament optical fibers having a fused silica glass core, with a doped silica cladding and polyimide buffer. Each fiber is shielded by an opaque jacket (not shown). The fiber diameter is chosen to optimize the collection of scattered light, thus, is best chosen in view of the particular application. Typically, fibers having core diameters of approximately 400 to 700 microns are preferred. For use in a radioactive environment, fibers 50, 52 are selected for good radiation resistance.

The dimensions of probe 10 are preferably such as provide a suitable signal for analysis and minimize the amount of light that is reflected by inner surface 22. The optimum length of chamber 18 depends on the choice of optical fibers and the diameter of the chamber. Preferably, the length and diameter of chamber 18 are such that light cone 66 emitted by fiber 50 and diverging at an angle $\alpha$ does not strike inner surface 22 before reaching end surface 34. Thus, for a type of optical fiber with $\alpha=30°$, a 0.5" (about 1.3 cm) diameter chamber 18 is no more than approximately 0.9" (about 2.3 cm) long; for $\alpha=35°$, a 0.5" diameter chamber is no more than approximately 0.8" (about 2.0 cm) long.

The greater the amount of sample that is contained in chamber 18, the greater the Raman signal and greater the sensitivity of probe 10. Thus, the sensitivity may be increased by increasing the volume of chamber 18. However, any increase in sample volume is limited by the need to minimize the amounts of potentially hazardous materials that may be used with probe 10, and, where probe 10 is used in monitoring a process stream, the need to minimize any impact of the measurement on the process. The sensitivity may also be increased by raising the pressure of the sample held in chamber 18 to increase the number of light-scattering molecules in the chamber.

Figure 2:
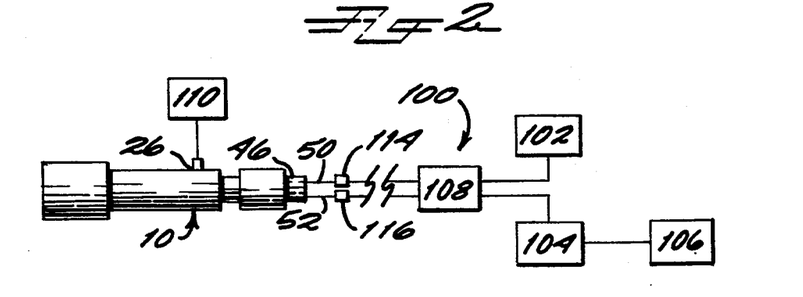
FIG. 2 is a schematic view of an apparatus for performing light scattering measurements according to the invention.

A schematic view of an apparatus for light scattering measurements according to the present invention is shown in FIG. 2. Apparatus 100 includes at least one probe 10, a light source 102, a spectrophotometer 104, and a computer 106. The proximal ends of fibers 50, 52 may be directly connected to source 102 and spectrophotometer 104, respectively. Alternatively, a plurality of probes may be placed in different locations, connected to a single light source 102 and spectrophotometer 104 via an optical multiplexer 108. A pump 110 feeds a sample into probe 10 via inlet fitting 26. Pump 110 is any device that is suitable for transferring a sample into chamber 18, and pressurizing chamber 18 to a predetermined pressure.

The exciting light produced by source 102 can be of any wavelength from UV to near-IR, but is preferably in the visible range. It is well known that the delta wavelength pattern of a typical Raman spectrum is independent of the wavelength of the exciting light. Although the intensity of the spectrum may be greatest at a particular exciting wavelength, for most analytes, usable Raman signals are obtainable over a wide range of exciting wavelengths. By way of example, gases such as $H_2$, $N_2$, $O_2$, $CH_4$, $CO_2$ and $CO$ have Raman spectra that are readily detectable at exciting wavelengths on the order of 500 nm. Of course, the wavelength of source 102 may be chosen to optimize the Raman signal of the particular analyte that is to be detected. Source 102 may be an air-cooled argon-ion laser with the plasma lines removed using a narrow-bandpass filter centered at 488 nm or 514 nm, a tunable laser to allow adjustment of the wavelength depending on the analyte to be detected, or some other type of laser that emits light of the desired wavelength.

Spectrophotometer 104 is any suitable type of spectrophotometer that responds to light in the wavelength range of interest, such as a fast scan spectrophotometer, diode array spectrophotometer, or a liquid nitrogen cooled charge coupled device (CCD) array detector. When an array detector is used, a sharply-focused image of each light-receiving fiber 52 is obtained on the detector array, allowing summing of the signals from a plurality of fibers without the inherent losses obtained by using additional external optics. In addition, array detectors provide the capability of using the same detector for monitoring several different probes 10 simultaneously.

Spectrophotometer 104 may include an analog-to-digital converter for digitizing the light signal received from probe 10. Alternatively, computer 106 may digitize the data. Computer 106 uses stored algorithms to process the digitized information and determine the constituents and concentrations of the sample. The results may be displayed in any convenient manner.

A reject filter 114 is in optical communication with fiber 50, between probe 10 and light source 102. Filter 114 allows only light in a narrow wavelength band around the exciting wavelength to pass into chamber 18. Filter 114 may also absorb at least a portion, and preferably most of the self-scattering light generated in fiber 50 by light from source 102. A pass filter 116 is in optical communication with fiber 52, in the light path between probe 10 and spectrophotometer 104. Filter 116 preferentially absorbs light in a narrow wavelength band around the wavelength of light source 102, but transmits substantially all light of other wavelengths. Thus, filter 116 removes at least a portion of the laser line at the spectrometer input optics.

Filters 114, 116 may be inline filters as shown in FIG. 2, positioned as close as possible to probe 10. If the process environment allows, filters 114, 116 preferably take the form of coatings over the distal ends of fibers 50, 52, respectively, shown as coatings 70, 72 in FIG. 1. Coatings 70, 72, if present, are preferably substantially nonreactive with the samples to be analyzed with probe 10.

In use, a sample to be analyzed is pumped into chamber 18 of probe 10. Exciting light from source 102 is transmitted by fiber 50 and directed through window 62 (if present) into chamber 18. The light strikes the sample molecules, causing at least a portion of the light to be scattered, and, to some extent, directed towards fiber 52. That portion of the exciting light which is not absorbed or scattered by the sample molecules before reaching coating 36 is substantially absorbed by the coating. Coating 24, if present, absorbs substantially all light reaching it, including all scattered light but that directed towards fiber 52. The light received by fiber 52 (including Raman-scattered light and non-Raman-scattered light) is transmitted to spectrophotometer 104, and computer 106 evaluates the resulting spectral data.

Computer 106 contains a stored library of calibration data obtained by measuring the Raman spectra (rotational, vibrational, or both) of a series of samples having known concentrations of the analyte(s) of interest, at a range of pressures. These data are analyzed by any of a number of chemometric techniques including Principal Components Regression (PCR), Partial Least Squares (PLS), Classical Least Squares (CLS), Multiple Least Squares (MLS), Multiple Linear Regression (MLR) and other techniques known in the art to model concentration-dependent and pressure-dependent variations in the spectra.

PCR and Partial Least Squares both model spectral data sets by constructing orthogonal vectors to describe the variance between the spectra in a set. In PCR analysis, the vectors are chosen to minimize the error in the spectral data. An unknown spectrum is decomposed to eigenvalues corresponding to each of the principal component regression vectors. To build a model, the eigenvalues of the spectra in a calibration data set are correlated with the known concentrations by any of a number of suitable methods such as Multiple Least Squares.

Partial Least Squares analysis assumes a linear relationship between the data and the concentrations/pressures. An unknown spectrum is analyzed by computing likenesses between the spectrum and the orthogonal vectors of the calibration data set, then summing the contribution to the concentration from each of the vectors. Spectrum residuals are computed by subtracting the likenesses of the vectors from the original spectrum. The number of vectors used to describe a given chemical system is determined by minimizing the predicted error of a set of spectra with known concentrations. Whether PCR, Partial Least Squares, or some other technique is used depends on the nature of the analyte to be detected, the wavelength range of interest and the type of spectrophotometer 104.

Figure 3:
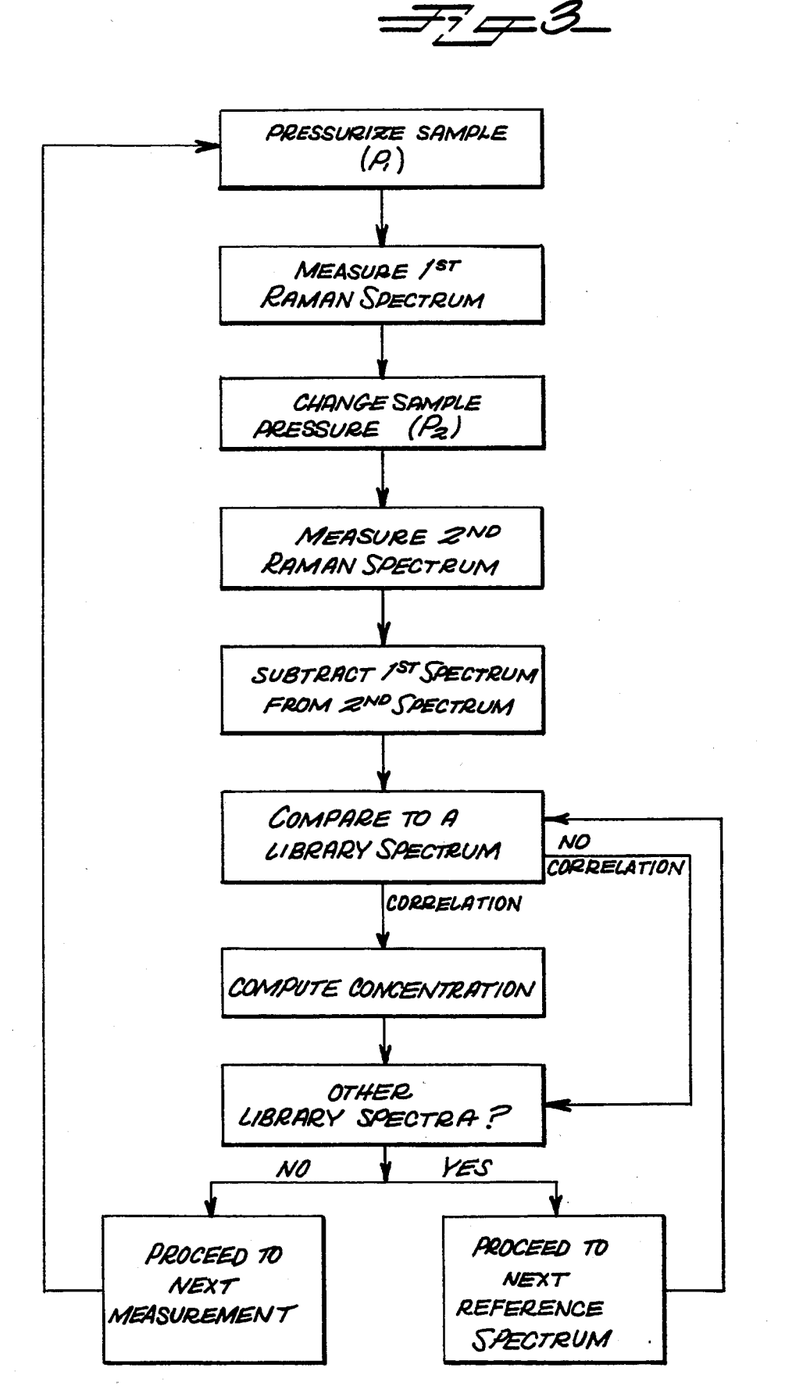
FIG. 3 is a flow chart of a method for determining the composition of a sample using the method of the present invention.

Using probe 10 and apparatus 100, samples are analyzed generally as indicated in FIG. 3. The constituents of a sample are determined as follows:

1. Position a probe 10 in the region where the presence and concentration of an analyte (or analytes) is to be detected.

2. Using pump 110, admit a sample to chamber 18 and pressurize the chamber to a first sample pressure PI. The first pressure may be atmospheric pressure, or a lower or higher pressure if desired.

3. Measure a first Raman spectrum.

4. Change the sample pressure to a second value ($P_2$), preferably to approximately 5 atm or higher.

The higher the pressure in chamber 18, the greater the number of scattering molecules and the greater the Raman signal. For increased Raman signals with low-concentration gaseous samples, pressures up to approximately 1,500 psi (about 102 atm) or higher might be used, depending on the materials used for probe 10. The optimum pressure for any particular measurement depends on the nature and concentration of the analyte of interest.

5. Measure a second Raman spectrum.

6. Subtract the first spectrum from the second to obtain the Raman spectrum of the sample.

The Raman spectrum measured by spectrophotometer 104 is characteristic not only of the scattering molecules in the sample, but also of the apparatus used for the measurements, including sample chamber 18, fibers 50, 52 and filters 114, 116. In particular, the fibers themselves generate Raman signals as a result of exciting light passing through them, and the signal in light-receiving fiber 52 includes exciting light from source 102. Probe 10 substantially reduces the amount of exciting light reaching fiber 52, and filter 116 preferentially absorbs light having the same wavelength as the exciting light. However, the signal in fiber 52 contains predominantly background light. Typically, the Raman signal measured in Steps 4 and 5 constitutes on the order of 0.5% of the total signal in fiber 52.

In order to remove such effects, that part of the signal which is due to factors other than scattering from the sample molecules is subtracted from the measured spectrum. This is done by comparing a spectrum with the sample at pressure $P_2$ (Step 5), with a spectrum made with the same apparatus but with the sample at a different pressure $P_1$ (Step 3).

If desired, a blank sample such as nitrogen or an inert gas might be used in Steps 2 and 3. However, the concentration of any analyte of interest is usually so low that it is indistinguishable from background readings at atmospheric or lower pressures. In addition, measurements with other gases may be difficult or impossible when probe 10 is used, for example, in an industrial process environment or for environmental monitoring.

7. Compare the sample spectrum to the library data to determine the constituents of the sample.

A library search of the calibration data stored in computer 106 is performed to determine whether or not an analyte of interest is present. Thus, the delta wavelengths of the peaks in the sample spectrum may be compared to those of a reference Raman spectrum for a particular analyte. If the two spectra are similar, that analyte is present in the sample. Depending on the process environment, computer 106 may contain data on 5-10 or even fewer compounds, however, more data may be stored if needed.

If there is no correlation, that analyte is not present in the sample in a detectable amount and the analysis is terminated. Proceed to the next spectrum measurement (Step 1), or, where more than one analyte is to be detected, compare the measured difference spectrum to the reference Raman spectrum of the other analytes of interest to determine whether those analytes are present in the sample.

8. If a correlation is found, analyze the sample Raman spectrum to determine the concentration of the analyte.

The measured and library spectra may be compared directly, for example, by comparing the intensities of the peaks in the measured and library spectra. Alternatively, the first derivative (or second and higher-order derivatives) may be computed and used in the analysis. Calibration data for one or more analytes of interest may be stored in computer 106. Therefore, the procedure described above may be used to compare a single measured spectrum with as many library spectra as are needed to determine the composition of a sample. Once an analyte is found to be present, the concentration of that analyte is found using the stored calibration data. As will be evident, the relative proportions of the constituents of a sample remain constant even though the pressure of the sample is changed for the second measurement (Step 5). However, the intensity of the Raman signal is greater since there are more molecules to scatter light.

The Raman spectrum of one of the isotopes of hydrogen (protium) was measured using the apparatus of FIG. 2. A 5-watt argon-ion laser (Spectra Physics 2020) was used as source 102, with the plasma lines removed using a 2-nm bandpass filter (filter 114) centered at 488 nm. Fibers 50, 52 of probe 10 were 600 micron silica core with doped silica cladding and a polyimide buffer. The light collected by fibers 52 was passed through a holographic notch filter (filter 116) to remove the laser line at the spectrometer input optics. The spectrophotometer system (106) consisted of a 0.5 m F/4 spectrometer (Spex 500M) with a liquid nitrogen cooled 512×512 CCD array detector (EG&G PARC).

Figure 4:
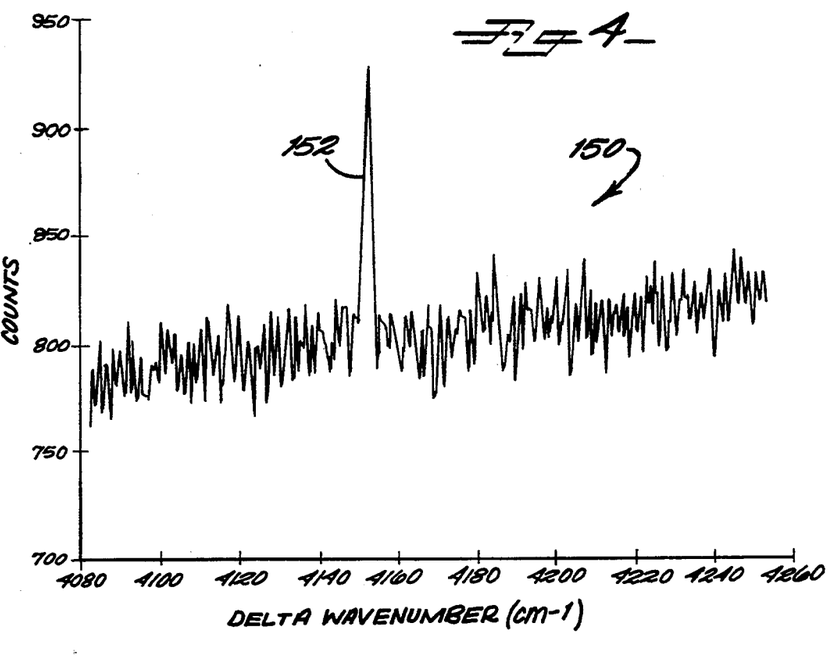
FIG. 4 shows the vibrational spectrum of 1% hydrogen in nitrogen at 800 psi (approximately 54 atm), obtained with the apparatus of FIG. 2.

FIG. 4 shows a vibrational spectrum 150 of a mixture containing 1 vol. % protium ($H_2$) in nitrogen ($N_2$). Two spectra were measured, the first at approximately atmospheric pressure and the second at a pressure of 800 psi (approximately 54 atm). The sample Raman spectrum was computed as described in Step 6. The spectrum consists of a single peak 152 at 4160 $cm^{-1}$ from the laser line (488 nm). Since peak 152 is so far separated from the intense line of source 102, there is little overlap and consequently little likelihood of overlap with Raman lines from other gases that may be present in the sample.

Figure 5:
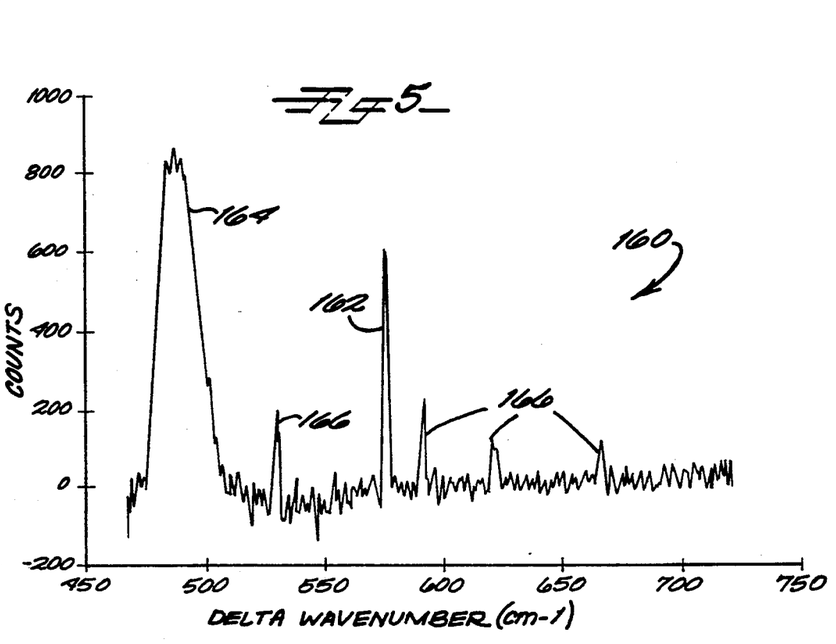
FIG. 5 shows the rotational spectrum of 1% hydrogen in nitrogen at 600 psi (approximately 41 atm), obtained with the apparatus of FIG. 2.

FIG. 5 shows a rotational Raman spectrum 160 of a mixture containing 1 vol. % protium in $N_2$, at a pressure of 600 psi (approximately 41 atm). A peak 162 represents the second rotational line of hydrogen, 580 $cm^{-1}$ from the laser line. A broad peak 164 at approximately 488 $cm^{-1}$ is the remnants of the laser line after filtering through the holographic notch filter (filter 116); the other, smaller peaks 166 are plasma lines from source 102 that are not completely removed by filters 114 and 116. This region of the spectrum is useful for determining ratios of the isotopes of hydrogen in a mixture since the other isotopes of hydrogen (deuterium, tritium) have rotational Raman lines in this region.

Both the vibrational and rotational Raman lines of pure hydrogen are easily observed using the above-described apparatus, but the vibrational line (FIG. 4) is better suited for detection due to its isolation from the laser line.

Due to its ability to distinguish many analytes based on their rotational or vibrational "fingerprint" energy levels, Raman spectroscopy is useful for process control applications and environmental monitoring. By using multiplexing or a spectrometer with multiple inputs, only probe 10 needs to enter the process environment, and several points can be sampled using the same laser, spectrometer and computer system. If desired, probe 10 can be used for other types of light scattering measurements such as fluorescence or luminescence.

Probe 10 and apparatus 100 allow remote, in-situ analysis of a wide variety of gaseous samples. Gases amenable to analysis include but are not limited to the isotopes of hydrogen (protium, deuterium, tritium), $CO_2$, $CO$, $CH_4$, $O_2$, and $N_2$. Concentrations as low as 0.1% can be detected; lower concentrations may be detectable using enhanced techniques such as resonant Raman scattering or surface-enhanced Raman scattering.

It will be apparent to those skilled in the art that many changes and substitutions can be made to the preferred embodiment herein described without departing from the spirit and scope of the present invention as defined by the appended claims.

What is claimed is:

1. A probe for use in light scattering analyses of a sample, said probe for use with a source of light and a spectrophotometer, said probe comprising:

a probe body having an interior, an interior surface, and means formed in said probe body for admitting said sample into said interior, said sample in said interior having a pressure;

means for controlling said pressure;

first light-transmitting means for transmitting exciting light from said source into said interior, a first portion of said exciting light interacting with said sample to produce Raman-scattered light, a remaining portion of said exciting light producing non-Raman-scattered light in said interior;

second light-transmitting means for transmitting light from said interior to said spectrophotometer; and means for preventing a substantial portion of said non-Raman-scattered light from reaching said second light-transmitting means.

2. The apparatus as recited in claim 1, wherein said preventing means further comprises a light-absorbing coating carried by said interior surface.

3. The apparatus as recited in claim 1, wherein said preventing means further comprises:

a light-absorbing coating carried by said interior surface, said coating comprising:

an adhesive; and a quantity of carbon black particles mixed with said adhesive.

4. The apparatus as recited in claim 1, wherein said probe body further comprises a proximal end and a distal end, said distal end having an interior surface, said first and second light-transmitting means in optical communication with said proximal end, and wherein said preventing means further comprises a light-absorbing coating carried by said interior surface of said distal end.

5. The apparatus as recited in claim 1, wherein said first light-transmitting means further comprises at least one optical fiber having a proximal end and a distal end, said proximal end in optical communication with said source and said distal end in optical communication with said interior, and wherein said second light-transmitting means further comprises at least one optical fiber having a proximal end and a distal end, said proximal end in optical communication with said spectrophotometer and said distal end in optical communication with said interior.

6. The apparatus as recited in claim 1, wherein said probe body further comprises a proximal end and a distal end, said distal end having an interior surface, said first light-transmitting means in optical communication with said proximal end, and wherein said probe body is dimensioned so that diverging light emitted by said first light-transmitting means reaches said interior surface of said distal end before striking said interior surface of said probe body.

7. A probe for use in light scattering measurements of a sample containing molecules, said probe for use with a source of light and a spectrophotometer, said probe comprising:

a probe body having an interior, an interior surface, and an inlet;

at least one light-transmitting fiber having a proximal end and a distal end, said proximal end in optical communication with said source and said distal end in optical communication with said interior, said at least one light-transmitting fiber transmitting exciting light from said source into said interior, a portion of said exciting light interacting with said sample molecules to produce Raman-scattered light, a remaining portion of said exciting light interacting with said sample molecules and said interior surface to produce non-Raman-scattered light;

at least one light-receiving fiber having a proximal end and a distal end, said proximal end in optical communication with a spectrophotometer and said distal end in optical communication with said interior, said light-receiving fiber transmitting light from said interior to said spectrophotometer; and a coating carried by said interior surface, Said coating including an adhesive and a quantity of carbon black particles carried by said adhesive, said coating preventing a substantial portion of said non-Raman-scattered light from reaching said at least one light-receiving fiber.

8. The apparatus as recited in claim 7, wherein said interior further comprises a proximal end and a distal end, said distal ends of said at least one light-transmitting fiber and said at least one light-receiving fiber in optical communication with said proximal end, said distal end of said interior having an interior surface, and wherein said coating is carried by said interior surface of said distal end.

9. The apparatus as recited in claim 7, wherein a sample in said interior has a pressure, further comprising means in fluid communication with said inlet for controlling said pressure.

10. The apparatus as recited in claim 7, wherein said source of light has a wavelength, further comprising a filter in optical communication with said at least one light-receiving fiber, said filter absorbing at least a portion of light having said wavelength.

11. The apparatus as recited in claim 7, wherein light passing through said at least one light-transmitting fiber interacts therewith to produce Raman-scattered light having at least one wavelength, further comprising a filter in optical communication with said light-transmitting fiber, said filter absorbing at least a portion of light having said at least one wavelength.

12. The apparatus as recited in claim 7, wherein said distal ends of said at least one light-transmitting fiber and said at least one light-receiving fiber are adjacent and parallel.

13. The apparatus as recited in claim 7, wherein said distal ends of said at least one light-transmitting fiber and said at least one light-receiving fiber are grouped in a bundle, said light-receiving fibers surrounding said light-transmitting fiber.

14. The apparatus as recited in claim 7, further comprising means in operative connection with said inlet for preventing particles from entering said interior.

15. The apparatus as recited in claim 7, further comprising a window positioned just beyond said distal ends of said light-transmitting and said light-receiving fibers, said window preventing contact of said fibers with a sample contained in said interior.

16. The apparatus as recited in claim 7, wherein said probe body further comprises a proximal end and a distal end, said distal end having an interior surface, said distal end of said at least one light-transmitting fiber in optical communication with said proximal end, and wherein said probe body is dimensioned so that diverging light emitted by said least one light-transmitting fiber reaches said interior surface of said distal end before striking said interior surface of said probe body.

17. A method for detecting the presence and concentration of an analyte in a sample, said sample having a pressure, said method comprising the steps of:

directing exciting light into said sample so that at least a portion of said exciting light interacts with said sample to produce Raman-scattered light, a remaining portion of said exciting light producing non-Raman-scattered light;

transmitting at least a portion of said Raman-scattered light to a spectrophotometer with an optical fiber, while preventing at least a portion of said non-Raman-scattered light from reaching said optical fiber;

measuring a first Raman spectrum from said transmitted light, said pressure having a first value;

changing said pressure of said sample to a second value;

measuring a second Raman spectrum from said transmitted light; and comparing said first and said second Raman spectra to determine said presence and said concentration of said analyte.

18. The method as recited in claim 17, wherein said analyte has a reference Raman spectrum, and wherein said comparing step further comprises:

subtracting said first Raman spectrum from said second Raman spectrum to obtain a sample Raman spectrum; and comparing said sample Raman spectrum to said reference Raman spectrum to determine if said spectra match.

19. The method as recited in claim 17, wherein said analyte has a reference Raman spectrum having at least one reference line with a delta wavelength and an intensity, and wherein said comparing step further comprises:

subtracting said first Raman spectrum frown said second Raman spectrum to obtain a sample Raman spectrum, said sample spectrum having at least one Raman line with a delta wavelength and an intensity;

comparing said delta wavelengths of said at least one Raman line and said at least one reference line to determine if said sample spectrum and said reference spectrum match; and comparing said intensities of said at least one Raman line and said at least one reference line to determine said concentration of said analyte in said sample.

20. The method as recited in claim 17, wherein said light-directing step further comprises the step of passing said exciting light into a chamber containing said sample, said chamber having a light-absorbing interior surface, said surface absorbing at least a portion of light not reaching said optical fiber.

* * * * *